(12) United States Patent
Kuester, III (10) Patent No.: US 7,144,402 B2
(45) Date of Patent: Dec. 5, 2006

(54) VASCULAR CLAMP

(75) Inventor: William Frank Kuester, III, Blaine, MN (US)

(73) Assignee: Synovis Life Technologies, Inc., St. Paul, MN (US)

( * ) Notice: Subject to any disclaimer, the term of this patent is extended or adjusted under 35 U.S.C. 154(b) by 136 days.

(21) Appl. No.: 10/462,494

(22) Filed: Jun. 16, 2003

(65) Prior Publication Data

US 2004/0254596 A1    Dec. 16, 2004

(51) Int. Cl.
*A61B 17/22*    (2006.01)
(52) U.S. Cl. ...................................... 606/158; 606/157
(58) Field of Classification Search ................ 606/151, 606/157, 158, 205–207; D24/143; 81/405
See application file for complete search history.

(56) References Cited

U.S. PATENT DOCUMENTS

| | | | |
|---|---|---|---|
| 3,805,792 A | 4/1974 | Cogley | 128/325 |
| 3,911,926 A | 10/1975 | Peters | 128/325 |
| 4,165,747 A | 8/1979 | Bermant | 128/334 C |
| 4,324,248 A * | 4/1982 | Perlin | 606/158 |
| 4,478,219 A | 10/1984 | Rozario et al. | 128/325 |
| D276,461 S * | 11/1984 | Scanlan et al. | D24/143 |
| 4,556,060 A | 12/1985 | Perlin | 128/325 |
| 4,777,950 A | 10/1988 | Kees, Jr. | 128/325 |
| 4,800,879 A | 1/1989 | Golyakhovsky et al. | 128/325 |
| 4,815,466 A | 3/1989 | Perlin | 128/325 |
| 4,929,240 A | 5/1990 | Kirsch et al. | 606/151 |
| 4,931,058 A | 6/1990 | Cooper | 606/158 |
| 4,932,955 A * | 6/1990 | Merz et al. | 606/158 |
| 4,976,721 A * | 12/1990 | Blasnik et al. | 606/157 |
| 5,011,487 A | 4/1991 | Shichman | 606/158 |
| 5,074,869 A | 12/1991 | Daicoff | 606/158 |
| 5,103,839 A | 4/1992 | Shichman | 128/898 |
| 5,618,307 A * | 4/1997 | Donlon et al. | 606/205 |
| 5,683,405 A | 11/1997 | Yacoubian et al. | 606/158 |
| 5,733,295 A | 3/1998 | Back et al. | 606/158 |
| 5,944,729 A * | 8/1999 | Blake | 606/205 |
| 5,984,934 A * | 11/1999 | Ashby et al. | 606/151 |
| 6,502,482 B1 * | 1/2003 | Putsch et al. | 81/405 |

OTHER PUBLICATIONS

Ikuta, Yoshikazu "Microvascular Double Clamp" *Journal of Reconstructive Microsurgery* vol. 1, No. 1 pp. 41-43 (Jul. 1984).
Yoshii, Takashi, et al. "A New Disposable Microvascular Double Clip" *Journal of Reconstructive Microsurgery* vol. 3 No. 2 pp. 133-136 (Jan. 1987).
Narayanan, K et al. "A New Variable-Pressure Microvascular Clamp" *Microsurgery* vol. 9, No. 1 pp. 52-54 (1988).
Smahel, Jiri, et al. "New Disposable Microvascular Clamp" *Microsurgery* vol. 6, No. 2 pp. 129-131 (1985).

(Continued)

*Primary Examiner*—Julian W. Woo
(74) *Attorney, Agent, or Firm*—Fredrikson & Byron P.A.

(57) ABSTRACT

A vascular clamp and a method for temporarily occluding a vessel. The vascular clamp comprises two jaws, two handles, and a pivoting point. A biasing mechanism is positioned between the handles for biasing the handles apart so that a closing force is imparted along the length of the jaws. The pivoting points pivotally connect the jaws together and are also configured to allow one jaw to be lifted relative to the other jaw. The method of temporarily occluding a blood vessel comprises the steps of providing a vascular clamp as described above and positioning the clamp about a blood vessel.

19 Claims, 8 Drawing Sheets

OTHER PUBLICATIONS

Govita, A. "Simplified Microvascular Clamps" *British Journal of Plastic Surgery* pp. 347-348 (1989).

De Carolis, Vincente, et al. "A Simple Adjustable Microvascular Clamp With a Controllable Gentle Occlusion Mechanism" *Plastic and Reconstructive Surgery* vol. 70, No. 1 pp. 100-103 (Jul. 1989).

Stark, Ron H. et al. "A New Microvascular Clamp for the Production of Experimental Ischemia" *Microsurgery* vol. 5, No. 4 pp. 202-206 (1984).

Thurston, J. Bradley et al. "A Scanning Electron Microscopy Study of Micro-Arterial Damage and Repair" *Plastic and Reconstructive Surgery* vol. 57, No. 2 pp. 197-203 (Feb. 1976).

Gertz, S. David, et al. "Endothelial Cell Damage by Temporary Arterial Occlusion with Surgical Clips" *Journal of Neurosurgery* vol. 45 (Nov. 1976).

Yanase, Yoshiaki, et al. "An Experimental Study on Traumatic Charges in Microvessels Produced by Pressure Clamping" *The Australian and New Zealand Journal of Surgery* vol. 50, No. 4 (Aug. 1980).

Stamatopoulos, C., et al. "Microvascular Damage Caused by the Application of Surgical Micro Clips: The Effects of Pressure and Time" *International Journal of Microsurgery* vol. 2, No. 3-4 (Dec. 1980).

Yoshikau, Ikuta "Microvascular Double Clamp Type A-II" *Journal of Reconsturctive Microsurgery* vol. 1., No. 1 (Jul. 1984).

Product Literature for MicroClapms by Acland, [online], 2002 [retrieved on Aug. 22, 2003] Retrieved from the Internet: <URL:http://www.microsurgery.ch/English/products/vclamps/index/.html>.

Product Literature for Stealth™ Clips by Applied Medical [online], 2002 [retrieved on Aug. 22, 2003]. Retrieved from the Internet: <URL:htt://www.appliedmed.com/products-information/cardiac-vascular_stealth.htm>.

Product Literature for Novaclip™ Atraumatic Spring Clips by Novare Surgical Systems, Inc. [online ] 2002 [retrieved on Aug. 22, 2003] Retrieved from the Internet: <URL: http://www.novaresurgical.com/productline/prodline-clips.cfm>.

Product Literature for Greyhound™ Adjustable Spring Clip by Novare Surgical Systems, Inc. [online] 2002 [retrieved on Aug. 22, 2003] Retrieved from the Internet: <URL: http://www.novaresurgical.com/productline/prodline-clips.cfm.

Product Lietrature for BEAR™ Vessel Clamps by AROSurgical [online] [retrieved on Aug. 22, 2003] Retrieved from the Internet: <URL:http://www.arosurgical.com/vessel_clamp_detail.htm>.

Product Order for VAS Clamps by Microsurgery, Inc. [online], [retrieved on Aug. 22, 2003] Retrieved from the Internet: <URL:http://www.microsurgeryusa.com/productc.html.>.

Product Literature for Scanlan Vascu-Statt single-use bulldog clamps [online] [retrieved on Aug. 22, 2003] Retrieved from the Internet: <URL: http://www.scanlaninternational.com/disposable/vascustatt/index.html.>.

Product description for Biover Microvascular Clamp [online] [retrieved on Aug. 22, 2003] Retrieved from the Internet: <URL:http://www.synovismicro.com/default.cfm?PID+13.13>.

* cited by examiner

VASCULAR CLAMP

FIELD OF THE INVENTION

The present invention relates generally to vascular clamps. More specifically, the present invention relates to microvascular clamps for the temporary occlusion of small blood vessels.

BACKGROUND OF THE INVENTION

Over the years, several different devices have been developed to temporarily occlude blood vessels during surgery. These devices are widely varied and include many different configurations. Clamps have become an increasingly popular device of choice and a wide variety of clamp types have been developed for use in vascular surgery.

Clamps are available in both large and small sizes. Larger clamps typically have large shafts or handles and are most suitable for occluding larger blood vessels in surgery procedures where sufficient space is available at the surgical site. Small surgical clamps are ideal for use with smaller vessels in microvascular surgery where little space is provided.

Popular small clamps include "bulldog" clamps. "Bulldog" clamps are small clamps that are applied to a blood vessel with the thumb and forefinger or with another surgical instrument such as forceps or an applier. The clamps are then left on the blood vessel until they need to be removed. Two known reusable "bulldog" clamps include the Acland clamp (distributed by S&T located in Switzerland) and the VAS clamp (distributed by Microsurgery Instruments, Inc. from Bellaire, Tex.). Other known disposable bulldog clamps include the BEAR™ vessel clamp (Arosurgical Instruments Corporation of Newport Beach, Calif.), the Biover microvascular clamp (distributed by Biover AG of Switzerland), and the Vascu-Statt® clamp (distributed by Scanlan International, Inc. located in St. Paul, Minn.).

Bulldog clamps typically include two jaws each having handles and connected together at a pivot point. Some clamps also include a means, such as a spring, for biasing the handles against each other and thereby imparting a closing force between the jaws (hereinafter, "biased clamps"). Typically, a spring is positioned between the handles to bias the handles away from each other and to impart a closing force between the jaws. When a surgeon desires to open the jaws, the handles can be pushed together against the biasing of the spring to cause the jaws to open. Known clamps that include a spring are the STEALTH™ surgical clip (distributed by Applied Medical Resources, Inc. located in Rancho Santa Margarita, Calif.) and the Novaclip™ (distributed by Novare Surgical Systems, Inc. located in Cupertino, Calif.). Other exemplary spring clamps are described in U.S. Pat. No. 3,805,792 to Cogley, U.S. Pat. No. 4,165,747 to Bermant, U.S. Pat. No. 4,931,058 to Cooper, and U.S. Pat. No. 5,683,405 to Yacoubian et al., the entire teachings each of which are herein incorporated by reference. While all of these are varied in their designs and configurations, all employ a spring to aid in creating a closing force of the jaws about a vessel. Spring clamps are especially advantageous in that they are easy to use during surgery.

One problem associated with biased clamps is that the closing force exhibited by the jaws may cause damage to the vessel. For example, the closing force may be too strong for the particular vessel used, so that the jaws exhibit a pinching and crushing effect on the vessel. Also, when the jaws of most clamps are in a closed position about a blood vessel, the contact surfaces of the jaws are not maintained in a parallel relationship along the length of the jaws. Rather, the contact surfaces of each jaw become more and more spaced apart along the length of the jaws and over the diameter of the blood vessel. As a result, the closing force tends to vary along the length of the jaws, with the closing force being the strongest at the position closest to the jaw handles and being the weakest at the position farthest from the jaw handles. When used on a blood vessel, the section of the vessel held by the area of the jaw having the strongest closing force will be pinched more than the vessel section held by the area of the jaw having the weakest closing force. In either case, these overly strong or uneven closing forces may result in permanent occlusion of, or traumatic damage to, the vessel.

Others have tried to minimize the potential for vessel damage by modifying the closing force of the clamps on the vessels. For example, some have developed clamps that include mechanisms for adjusting the closing force during surgical use (hereinafter "adjustable clamps"). These adjusting mechanisms allow a surgeon to change the closing force to conform to the particular type and size of the vessel being occluded. Known adjustable clamps are described in U.S. Pat. No. 5,011,487 to Schichman, U.S. Pat. No. 5,103,839 to Schichman, and U.S. Pat. No. 5,733,295 to Back et al. the entire teachings of each of which are herein incorporated by reference. Also, some adjustable clamps have employed jaws with contact surfaces having a substantially parallel relationship to one another, so that when adjusted, the clamps have a uniform closing force along the length of the jaws. An example of such an adjustable clamp is the Greyhound™ adjustable spring clip (distributed by Novare Surgical Systems, Inc.). While these adjustable clamps provide certain advantages, they are often more difficult to use during surgery than the biased clamps. It is time consuming and cumbersome for a surgeon to have to adjust the closing force, particularly during the wet and slippery conditions of surgery. Adjustable clamps also tend to be more susceptible to operator error than the biased clamps which have a preset closing force.

Therefore, it would be desirable to provide a clamp incorporating the ease of use associated with the non-adjustable, biased clamps as well as the ability to ensure that the closing forces are uniform along the length of the jaws associated with the adjustable clamps. It would be particularly desirable to provide a biased clamp having contact surfaces that are maintained in a substantially parallel relationship when positioned about a blood vessel, so that uniform closing forces will be imparted along the length of the jaws and over the diameter of the vessel.

SUMMARY OF THE INVENTION

The present invention provides a vascular clamp for temporarily occluding a blood vessel so that when the jaws of the clamp are placed around a vessel, the closing forces are uniformly distributed along the length of the jaws and over the diameter of the vessel. Because the present clamp imparts a uniform closing force, vessel occlusion is optimized and trauma to the vessel is minimized.

In preferred embodiments, the vascular clamp comprises two jaws, two handles, and a pivoting point. Each jaw contains a blood vessel contacting surface. A biasing mechanism is positioned between the two handles to bias the handles apart, causing the jaws to be biased towards one another. The biasing also causes a closing force to be imparted along the length of the jaws. In particularly preferred embodiments, the biasing mechanism is a spring. In other embodiments, the biasing mechanism comprises a resilient member. The pivoting point pivotally connects the jaws together and is also adapted for allowing one jaw to be lifted relative to the other jaw when positioned on a blood vessel so that the closing force is distributed uniformly along the length of the jaws.

The jaws of the present invention will be described in terms of "opened", "closed", and "lifted" positions. The ability of the jaws to assume the lifted position is what enables the present clamp to impart uniform closing forces along the length of the jaws and over the diameter of a blood vessel. The pivoting point of the present invention provides for this lifting ability. When the jaws are in an opened position, the contact surfaces of the jaws are separated from one another but are not substantially parallel to one another. When the jaws are in a closed position, the contact surfaces are in contact with one another and are also substantially parallel to one another. When the jaws are in a lifted position, the contact surfaces are slightly spaced from one another and are also substantially parallel to one another. The lifted position can be thought of as a variation of the closed position where the contact surfaces are slightly spaced rather than contacting one another. Typically, when the present clamp is left alone in it's natural state, the jaws are maintained in a closed position. When force is applied to the clamp handles, the jaws assume an open position. When the clamp is positioned about a blood vessel and the force is released from the handles, the rigidity of the walls of the collapsed blood vessel causes the jaws to assume a lifted position.

The clamp members are connected together at a pivoting point. The pivoting points function to pivotally connect the clamp members together and also to provide the lifting functions of the present invention. In certain embodiments, the pivoting point comprises a hinge. In other embodiments, the pivoting point comprises a center portion having plates that are adapted to be slidably engaged within each other.

When it is desired to place the clamp about a blood vessel, the surgeon pinches the handles of each clamp member together, causing the jaws to open. The opened jaws are placed in position about a blood vessel and the pinching force on the handles is released, causing the jaws to close about the blood vessel. When the jaws are closed about the blood vessel, the rigidity of the collapsed walls of the blood vessel causes one clamp member to be lifted relative to the other. In the lifted position, the contact surfaces of the jaws are in a substantially parallel relationship and the closing force is uniformly distributed along the length of the jaws and over the diameter of the blood vessel.

DETAILED DESCRIPTION OF THE PREFERRED EMBODIMENTS

With reference to the FIGS. 1–9, the preferred embodiments of the vascular clamp will now be described.

Figure 1:
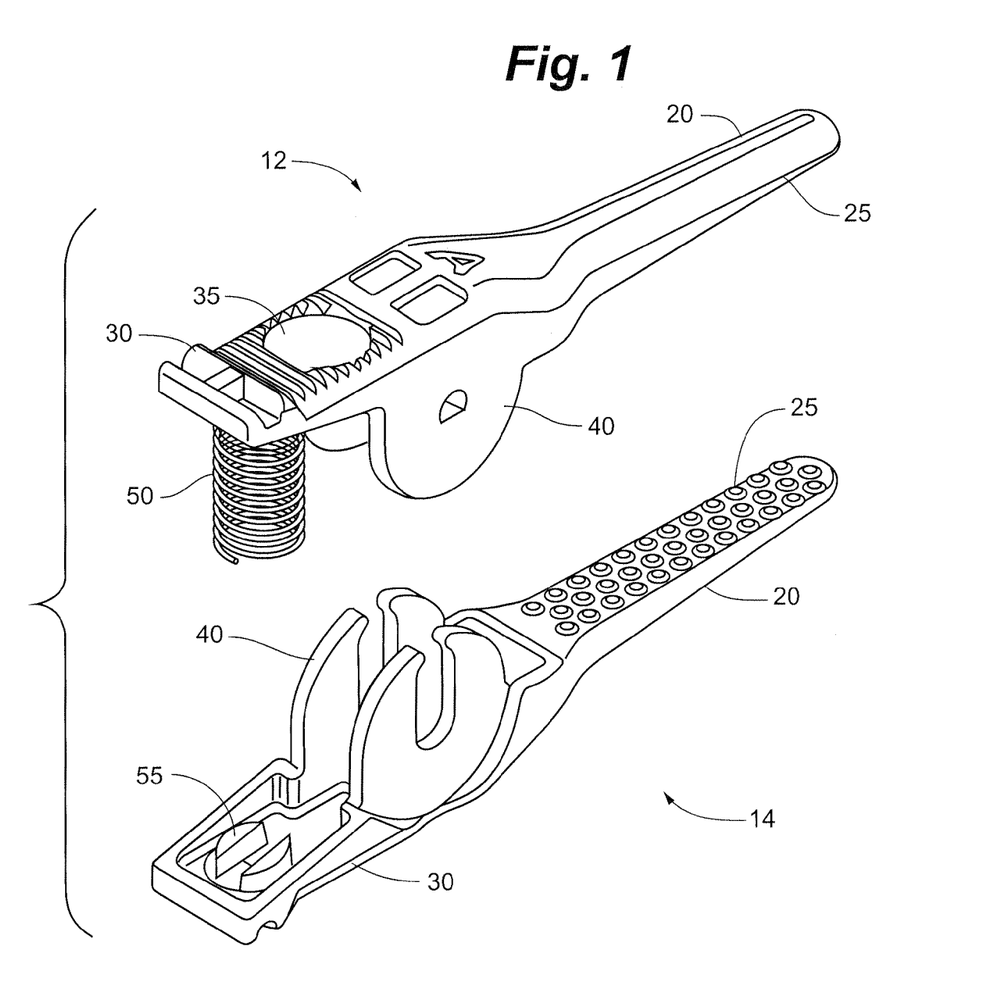
FIG. 1 is an exploded view of one embodiment of the clamp of the present invention.
Figure 2:
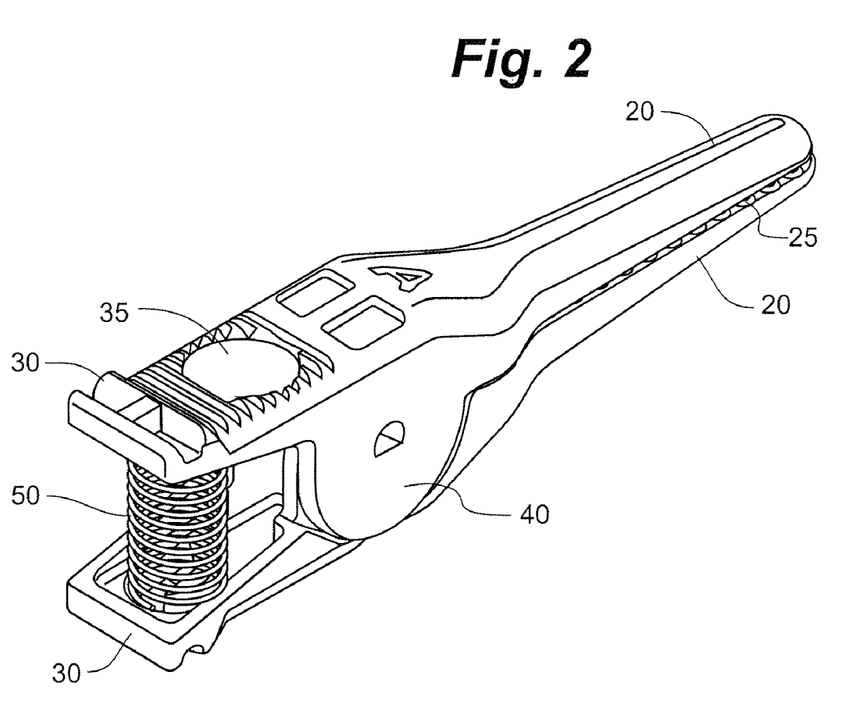
FIG. 2 is a perspective view of the clamp depicted in FIG. 1.
Figure 3:
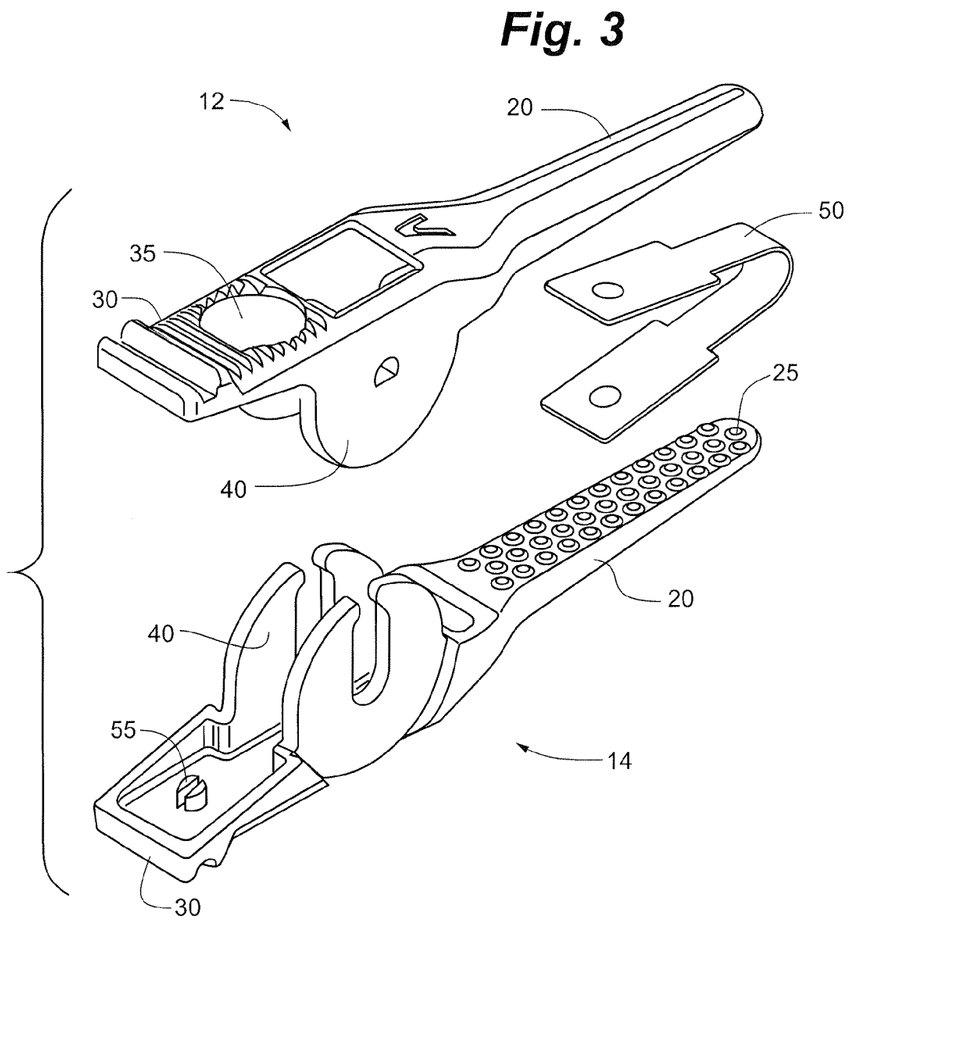
FIG. 3 is an exploded view of another embodiment of the clamp of the present invention.
Figure 4:
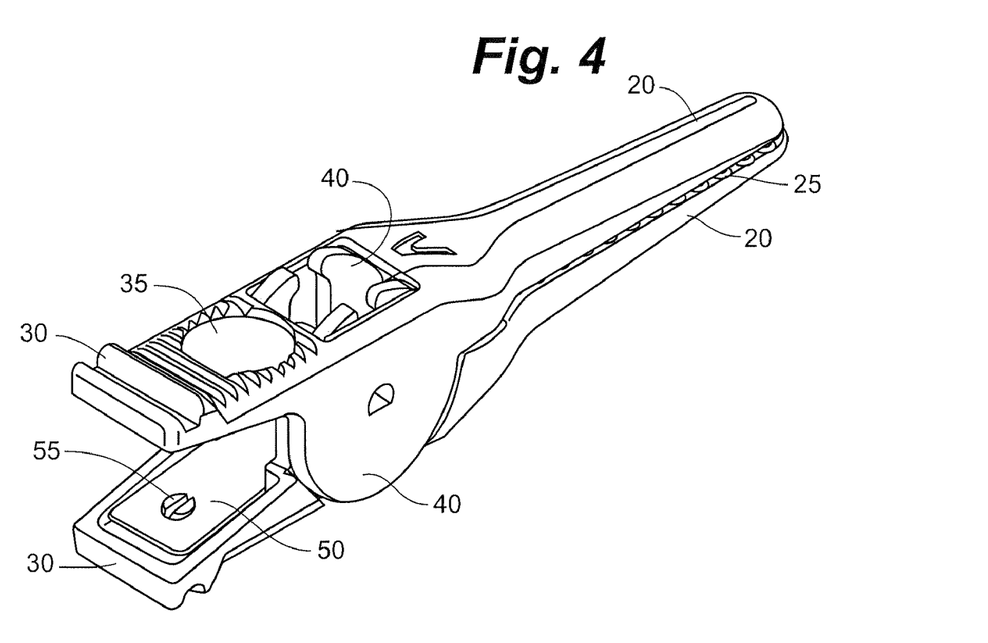
FIG. 4 is a perspective view of the clamp depicted in FIG. 3.
Figure 5:
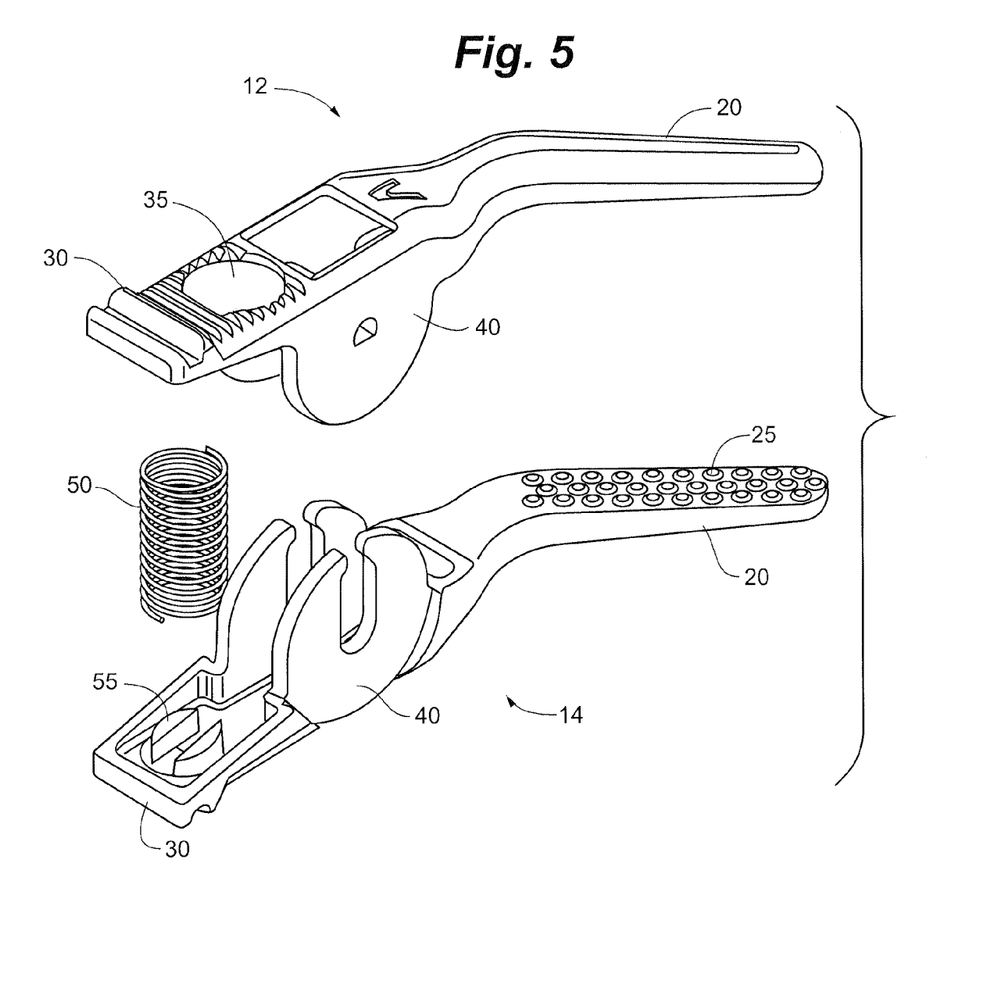
FIG. 5 is an exploded view of another embodiment of the clamp of the present invention.
Figure 6:
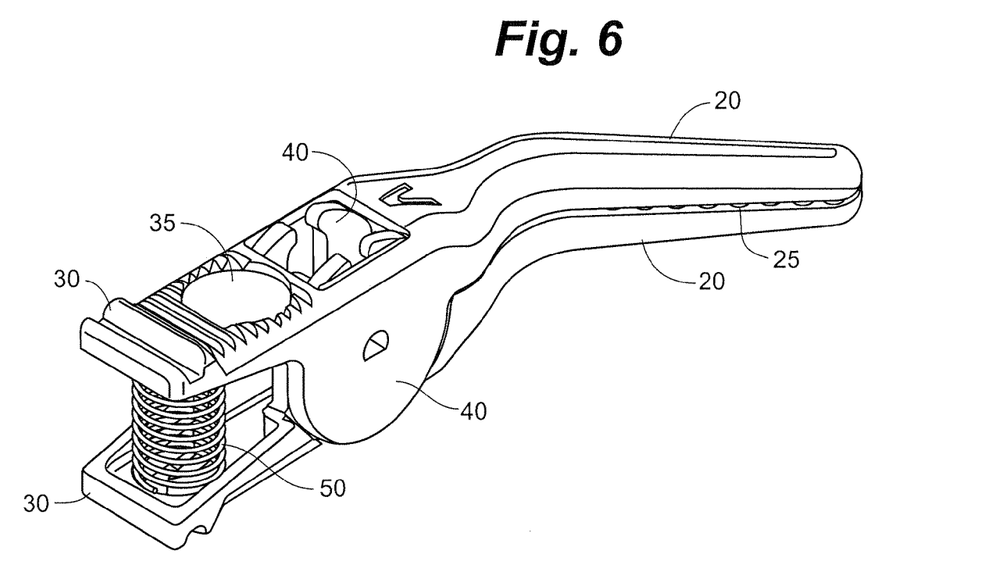
FIG. 6 is a perspective view of the embodiment depicted in FIG. 5.
Figure 7:
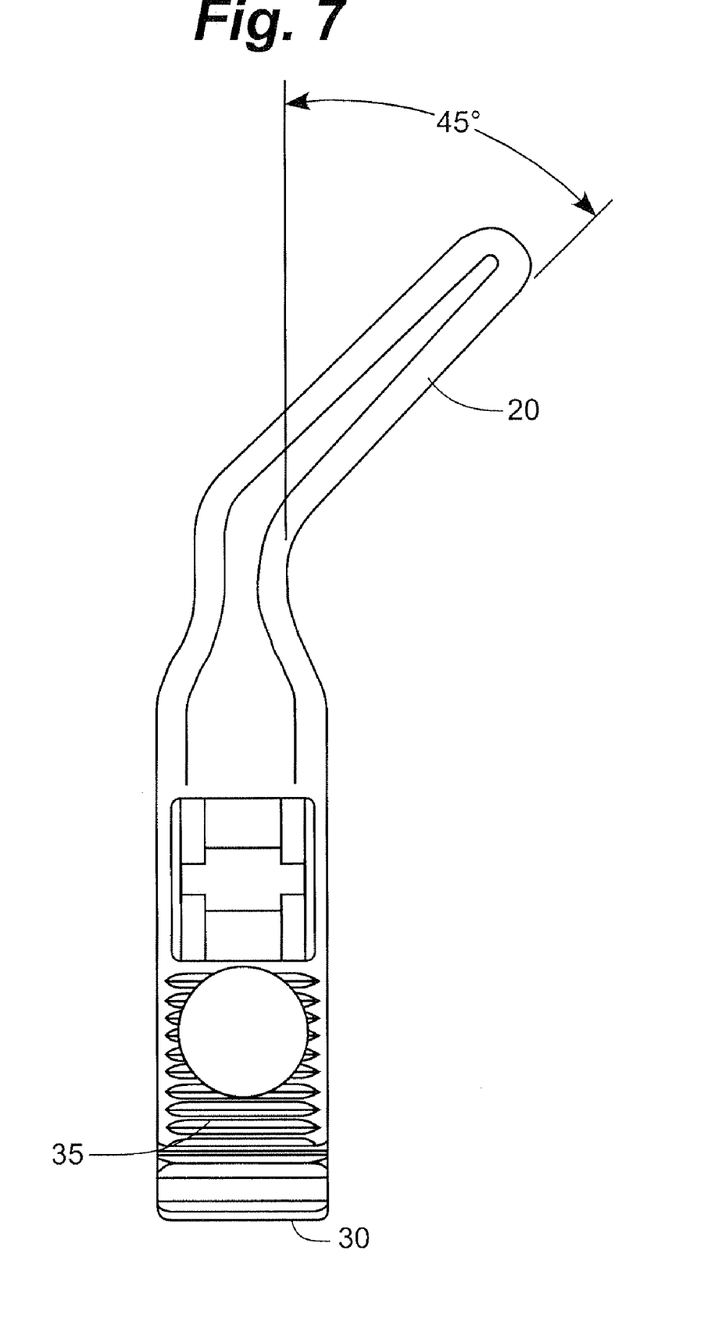
FIG. 7 is a top view of the embodiment depicted in FIG. 5.

The preferred vascular clamp includes two clamp members, 12 and 14. Each clamp member includes a handle 30, a pivoting point 40 and a jaw 20. FIGS. 1 and 3 show the clamp members in an unconnected form. FIGS. 2 and 4 show the clamp members in a connected form. The clamp members are connected together at their pivoting point 40.

The handles are adapted to be held by forceps or by hand (for example by fitting a user's thumb and forefinger). Each handle 30 also includes a handle surface 35. In some embodiments, the handle surface 35 is formed as a non-slip surface. The non-slip surface can have any suitable configuration to prevent slippage. For example, the surface can include grooves or ribs or the surface can be sandblasted to form a rougher surface having better gripping. The non-slip surface also makes it easier to grasp the handles during the slippery conditions of surgery.

Each jaw 20 is further provided with a blood vessel contact surface 25. This is the area along the inside of the jaws that will be in contact with a blood vessel. The contact surfaces 25 can also be in the form of non-slip surfaces. For example, the surfaces can include grooves or ribs or can be sandblasted to provide a rougher surface. The non-slip surfaces are beneficial in preventing the clamps from slipping off of the vessel during use. The contact surfaces 25 can also be provided with one or more layers and/or inserts mounted thereon. The one or more layers and/or inserts can be designed to provide a softer clamping surface, thereby minimizing the damage to the vessel by the clamp. The inserts can also be designed to provide a non-slip effect, thereby restricting movement of the vessel. The inserts can be either permanently or removably mounted and can include any suitable material. For example, the inserts can be in the form of pads made of an elastomeric material such as latex or thermoplastic elastomer.

Figure 8:
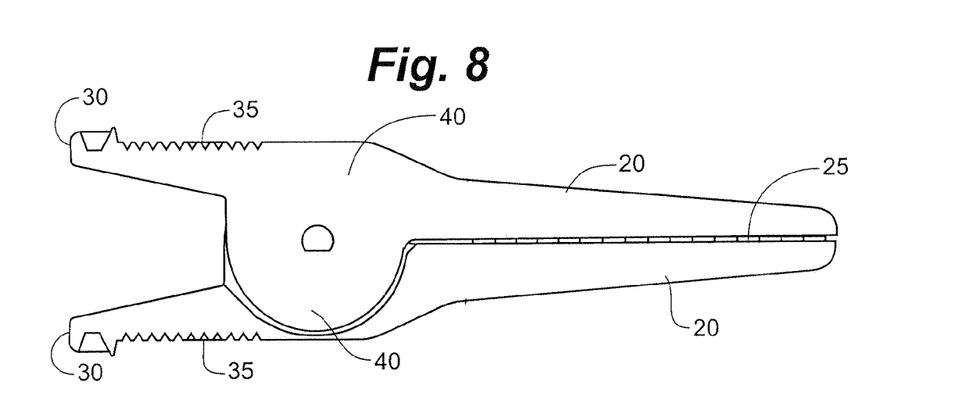
FIG. 8 is a side view of the clamp of the present invention showing the jaws in a closed position.
Figure 9:
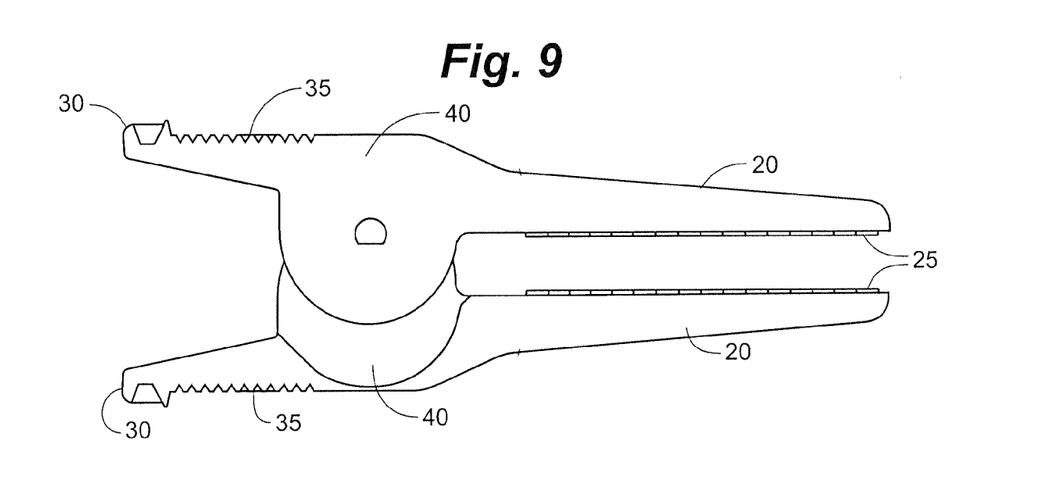
FIG. 9 is a side view of the clamp of the present invention showing the jaws in a lifted position.

The jaws 20 are movable between opened, closed and lifted positions. When the jaws 20 are in an open position, the contact surfaces 25 are separated from one another and are not substantially parallel to one another. When the jaws 20 are in a closed position, the contact surfaces 25 are in contact with one another and are also substantially parallel to one another. When the jaws 20 are in a lifted position, the contact surfaces 25 are slightly spaced from one another and are also substantially parallel to one another. FIG. 8 shows the jaws in a closed position. As seen by FIG. 8, when the jaws are closed, the jaw contact surfaces 25 are in a substantially parallel relationship. FIG. 9 shows the jaws in a lifted position. As seen by FIG. 9, when the jaws 20 are lifted, the jaws of the clamp become slightly spaced apart but the contact surfaces 25 are still maintained in a substantially parallel relationship.

The jaws 20 can also be provided in any suitable configuration, shape or size. For example, in the embodiments depicted in FIGS. 1–4 and 8–9, the jaws have a straight configuration. In the embodiments depicted in FIGS. 5–7, the jaws have a curved configuration. Clamps having curved jaws often facilitate the ease of positioning the clamp within the body. In the embodiment shown in FIG. 7, the jaws are curved to provide a suitable angle (e.g. a forty-five degree angle). The direction of closure of the jaws extends between adjacent points on the opposing jaws and varies depending on whether the jaws are straight or curved. If the jaws are straight, the direction of closure extends as a line along the length of the jaws. If the jaws are curved, the direction of closure extends as a curve. One with skill in the art will recognize that the jaws can be curved in any angle, direction or suitable configuration.

A biasing mechanism 50 is also provided for imparting a closing force along the length of the jaws 20. The biasing mechanism is typically placed in between the handle of the clamp. In the embodiments depicted in FIGS. 1–2 and 5–6, the biasing mechanism comprises a spring. In the embodiments depicted in FIGS. 3–4, the biasing mechanism comprises a resilient member. In some embodiments, each handle 30 further includes a connecting portion 60. The connecting portions 60 are designed to connect the biasing mechanism 50 in between the handles 30. The connecting portion 60 can be configured in any manner suitable for connecting a particular biasing mechanism 50 in between the handles. While preferred embodiments of the biasing mechanism are herein described, one of skill in the art will recognize that any biasing mechanism known in the art can be used.

In the case of the spring shown in FIGS. 1–2 and 5–6, the spring is adapted to be positioned between the handles 30. In this embodiment, a connecting portion 60 is provided on each handle 30 that is configured to connect a spring in between the handles. For example, in the embodiment shown in FIG. 1, the connecting portion 60 is in the form of a circular shoulder upon which a spring is inserted over and held into place upon each respective handle. The spring exerts an expanding force against each handle 30, thereby biasing the handles against one another and imparting a closing force along the length of the jaws 20. The spring has a predetermined compressive force so that a proper closing force is applied to the blood vessel by the clamp.

In the case of the resilient member shown in FIGS. 3–4, the resilient member is configured as an assembly consisting of two long parts or long shafts joined together at an end. The two shafts are biased against one another and are adapted to be positioned against each handle 30. In certain embodiments, a connecting portion 60 is provided on each handle 30 that is configured to connect each shaft of the resilient member to a handle. For example, the connecting portion 60 may be in the form of a shoulder and each shaft may contain an opening on upon which can be placed over the shoulder of the connecting portion and locked into place. Once the shafts are positioned against each handle, the shafts bias against one another and exert an expanding force against the handles, thereby biasing the handles against one another and imparting a closing force along the length of the jaws.

The present clamp further includes a pivoting point 40 adapted for pivotally connecting the jaws 20 together. In certain embodiments, the pivoting point comprises a hinge. In preferred embodiments (as shown in the Figures), the pivoting point comprises two center portions of each clamp member connected together in a manner so that the clamp members are pivoted together and one jaw can be lifted relative to the other jaw. For example, in preferred embodiments, two center portions are adapted to be slidably engaged within each other. This slidably engaged configuration allows for one center portion to be slidably lifted from the other center portion, thereby imparting the lifting functions of the present clamp. In the embodiments depicted by the Figures, the center portions are configured as a pair of parallel plates extending away from each clamp member. The spacing between the pair of parallel plates on one clamp member is wider than the spacing between the pair of parallel plates on the other clamp member. This allows for the wider pair of plates to slide over and along the outside of the other pair of plates.

While the plates can be in any suitable shape or formation, in the embodiment depicted in the Figures, each plate has a configuration of a half-circle or arc. One pair of parallel plates contain openings upon which a screw, bolt, bar, or any similar device can be inserted therethrough and the other pair of parallel plates contain elongated grooves upon which the same screw, bolt, or bar can also be inserted therethrough. Once the screw or bar device is positioned through both the openings and elongated grooves on the plates, the screw or bar device can be locked into place with a nut, cap or similar device. Thus, the clamp member containing the pair of plates with the screw inserted through the smaller openings can be moved upward and downward relative to the other clamp member as the screw is moved upward and downward along the elongated grooves. In this case, lifting of one jaw occurs when the screw is moved upward along the elongated grooves.

The present clamp can be either reusable or disposable. In a preferred embodiment, the clamp of the disposable type and the clamp components are made of any suitable biocompatible material. For example, the clamp components can be formed from a biocompatible polymer or copolymer such as polyvinyl chloride. The present clamp can also be made into a variety of sizes designed for use with a variety of blood vessels. For example, the clamp can be small (for use with vessels having a diameter of 0.5 to 1.0 mm), medium (for use with vessels having a diameter of 1.0 to 2.0 mm), or large (for use with vessels having a diameter of 2.0 to 5.0 mm). The clamp can also be color coded, providing easy identification of the type and size of the clamp. For example, artery clamps can be yellow and vein clamps can be green. This provides easy-to-identify color distinction between artery and vein clamps.

The clamp of the present invention can also be adapted to become part of a clamp apparatus. Clamp apparatuses are well known in the art and typically include an elongated rigid bar designed for accommodating a pair of clamps spaced apart along the bar. Guide brackets can also placed on each of the clamps to retain the clamps on the bar in traverse relation thereto and in a substantially coplanar relationship to one another. One or both of the guide brackets can be slidable upon the bar so that the spacing of the clamps can be adjusted. Suitable clamp apparatuses are described in U.S. Pat. Nos. 3,911,926, 4,165,747, and 5,011,487, the entire teachings of each of which are herein incorporated by reference. Apparatuses of this type are very helpful in microvascular surgery procedures, as they add to the precision of microvascular surgeries.

The clamp of the present invention can also be included as part of a kit. In one embodiment, one more clamps of the present invention are packaged along with the vascular monitoring tools described in applicant's own U.S. patent application Ser. No. 10/279,751, the entire teachings of which are herein incorporated by reference.

A further aspect of the invention involves a method of temporarily occluding a blood vessel during surgery. In certain embodiments, the method comprises the steps of providing a vascular clamp as described herein and positioning the clamp about a blood vessel. The present method can further include steps of selecting a vascular clamp and removing the clamp from the blood vessel.

The provided clamp will typically be of the type described above. For example, the clamp can be of the type comprising two jaws, two handles operatively biased against one another so that a closing force is imparted along the length of the jaws, and a pivoting point for pivotally connecting the jaws together and adapted for allowing one jaw to be lifted relative to the other jaw when positioned on a blood vessel so that the closing force is distributed uniformly along the length of the jaws.

In certain embodiments, several clamps are provided having a variety of sizes and being for use with a variety of blood vessels. In this embodiment, the method includes a further step of selecting a particular clamp for use with a blood vessel. Thus, the method comprises providing clamps having a variety of sizes and being for use with a variety of blood vessels, selecting a clamp for use with a blood vessel, and positioning the clamp about the blood vessel.

When positioning the clamp about a blood vessel, the surgeon applies a pinching force to the handles, thereby causing the jaws to assume an open position. The opened jaws are positioned about a blood vessel so that the blood vessel is in between the contact surfaces of each jaw. The surgeon then releases the pinching force exerted on the handles, causing the jaws to move towards a closed position. Once the contact surfaces of the jaws are in contact with the blood vessel, the rigidity of the blood vessel itself causes the jaws to assume a lifted position. In other words, one clamp member is lifted relative to the other clamp member. When the jaws assume this lifted position, the substantially parallel relationship of the contact surfaces allow the closing force to be distributed uniformly along the length of the jaws. This uniform distribution of closing force allows the blood vessel to be occluded evenly along its entire diameter. When removing the clamp, the surgeon reapplies a pinching force to the handles, causing the jaws to open, and removes the clamp from the blood vessel.

Although this invention has been described in terms of a preferred embodiments and methods, other embodiments and methods apparent to those of ordinary skill in the art are also within the scope of this invention. Accordingly, the scope of this invention is intended to be defined only by the claims that follow.

What is claimed is:

1. A vascular clamp for temporarily occluding a vessel, the vascular clamp comprising:
    two jaws;
    two handles having a biasing mechanism positioned therebetween for biasing the handles apart so that a closing force is imparted along the length of the jaws; and
    a pivoting point, comprising parallel plates extending away from each handle and adapted to be slidably engaged within each other, for pivotally connecting the jaws together and adapted for allowing one jaw to be lifted relative and substantially parallel to the other jaw when positioned on a blood vessel so that the closing force is distributed uniformly along the length of the jaws.

2. The vascular clamp of claim 1 wherein the pivoting point comprises a hinge.

3. The vascular clamp of claim 1 wherein the biasing mechanism comprises a spring.

4. The vascular clamp of claim 1 wherein the biasing mechanism comprises a resilient member.

5. The vascular clamp of claim 1 wherein the handles each have a non-slip surface.

6. The vascular clamp of claim 1 wherein the jaws have a straight configuration.

7. The vascular clamp of claim 1 wherein the jaws have a curved configuration.

8. The vascular clamp of claim 1 wherein the jaws each have a non-slip surface.

9. The vascular clamp of claim 1 wherein the jaws each have one or more inserts mounted on a contact surface thereof.

10. A method for temporarily occluding a vessel, the method comprising the steps of:
    providing a vascular clamp according to claim 1; and
    placing the jaws of the clamp about a blood vessel.

11. The method of claim 10 wherein the step of placing the jaws of the clamp about a blood vessel is accomplished by the steps of:
    applying a pinching force to the handles, causing the jaws to open;
    positioning the opened jaws about a blood vessel; and
    releasing the pinching force on the handles, causing the jaws to close on the blood vessel.

12. A vascular clamp for temporarily occluding a vessel, the vascular clamp comprising:
    two clamp members each having a handle and a jaw;
    a biasing mechanism positioned between the handles of each clamp member for biasing the handles apart so that a closing force is imparted along the length of the jaws; and
    a pivoting point for pivotally connecting each clamp member together and adapted for allowing one jaw to be lifted relative and substantially parallel to the other jaw when positioned on a blood vessel, so that the closing force is distributed uniformly along the length of the jaws, the pivoting point comprising a pair of parallel plates located on each clamp member and extending away therefrom, the pair of plates being adapted to be slidably engaged within each other so that one jaw can be slidably lifted from the other jaw.

13. The vascular clamp of claim 12 wherein the biasing mechanism comprises a spring.

14. The vascular clamp of claim 12 wherein the biasing mechanism comprises a resilient member.

15. The vascular clamp of claim 12 wherein the handles each have a non-slip surface.

16. The vascular clamp of claim 12 wherein the jaws have a straight configuration.

17. The vascular clamp of claim 12 wherein the jaws have a curved configuration.

18. The vascular clamp of claim 12 wherein the jaws each have a non-slip surface.

19. The vascular clamp of claim 12 wherein the jaws each have one or more inserts mounted on a contact surface thereof.

* * * * *